(12) United States Patent  
Ernst

(10) Patent No.: US 8,663,329 B2  
(45) Date of Patent: Mar. 4, 2014

(54) EXPANDABLE IMPLANT FOR MAMMALIAN BONY SEGMENT STABILIZATION

(76) Inventor: Mark J Ernst, El Paso, TX (US)

( * ) Notice: Subject to any disclaimer, the term of this patent is extended or adjusted under 35 U.S.C. 154(b) by 201 days.

(21) Appl. No.: 13/360,716

(22) Filed: Jan. 28, 2012

(65) Prior Publication Data

US 2013/0197642 A1 Aug. 1, 2013

(51) Int. Cl.
*A61F 2/44* (2006.01)

(52) U.S. Cl.
USPC ............................. 623/17.15; 623/17.16

(58) Field of Classification Search
USPC .............................. 606/105; 623/17.15, 17.16
See application file for complete search history.

(56) References Cited

U.S. PATENT DOCUMENTS 8,523,944 B2 * 9/2013 Jimenez et al. ............ 623/17.15

* cited by examiner

*Primary Examiner* — Andrew Yang
(74) *Attorney, Agent, or Firm* — Merle W. Richman, Esq.

(57) ABSTRACT

Embodiments of bony region stabilization implants are described generally herein including a controllable expandable implant for placement between two bony segments including vertebrae. Other embodiments may be described and claimed.

21 Claims, 13 Drawing Sheets

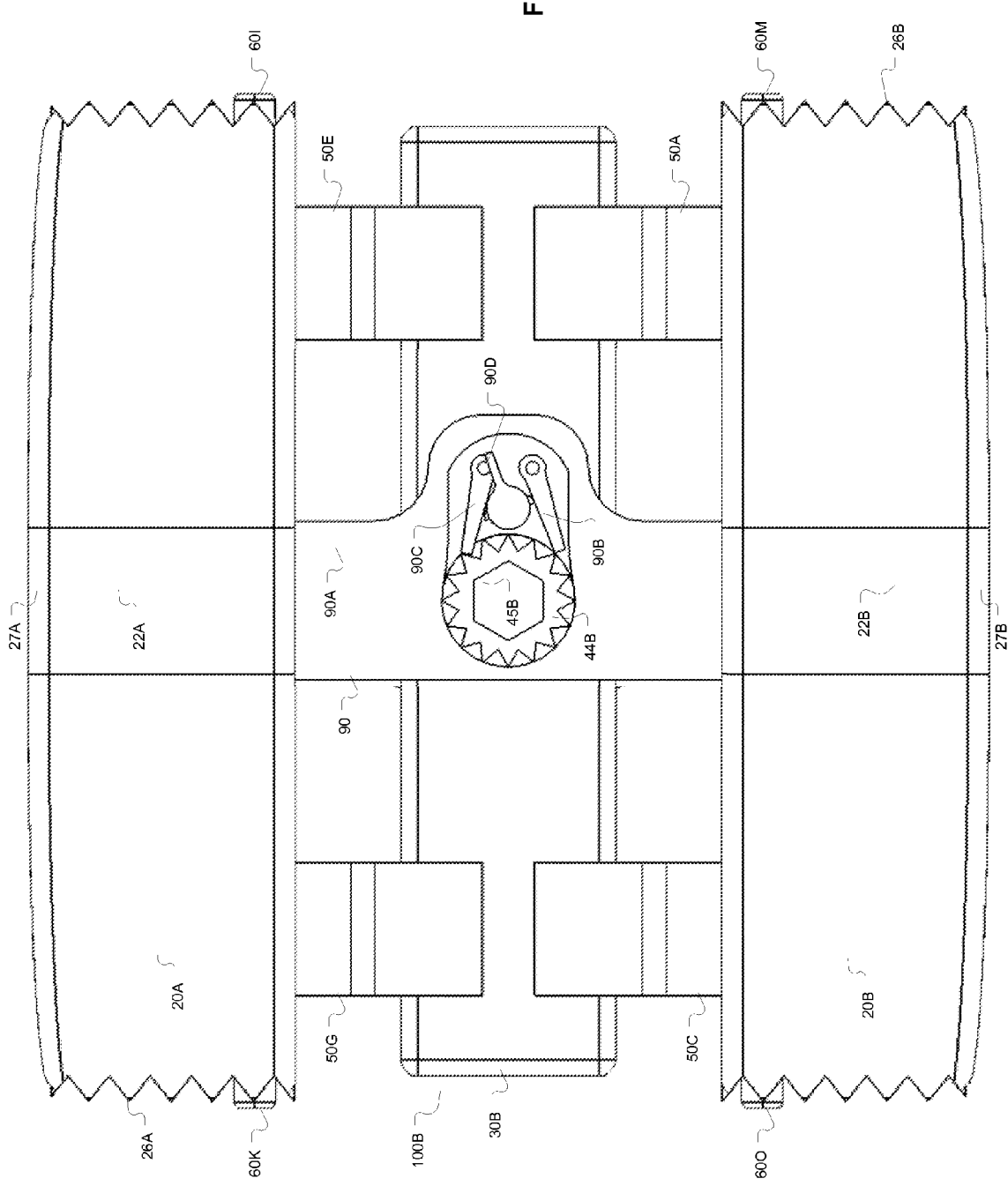

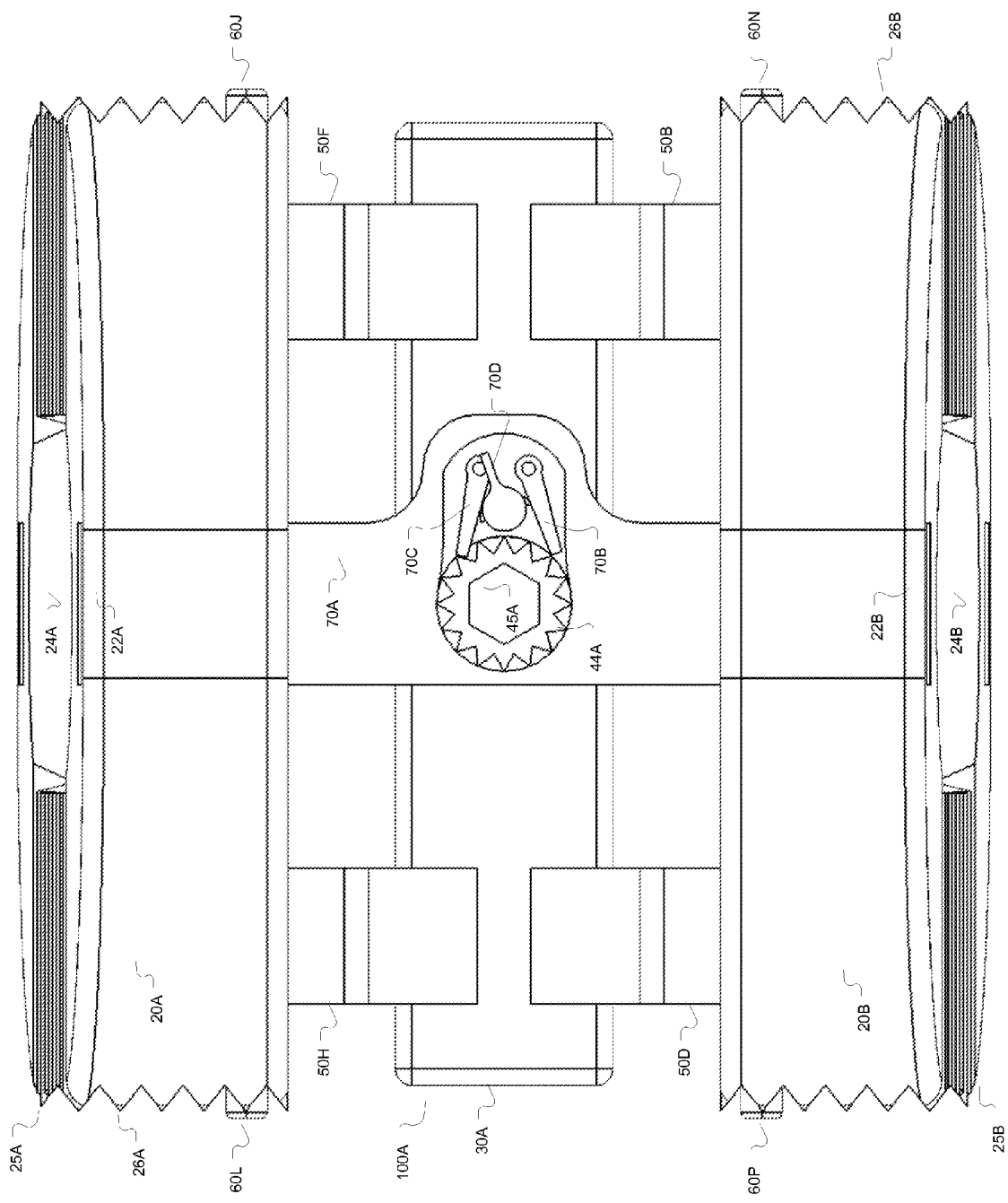

EXPANDABLE IMPLANT FOR MAMMALIAN BONY SEGMENT STABILIZATION

TECHNICAL FIELD

Various implant embodiments described herein relate generally to stabilizing mammalian bony segments, including fenestrated implants to stabilize one or more mammalian bony segments.

BACKGROUND INFORMATION

It may be desirable to stabilize one or more bony segments via one or more implants; the present invention provides such implants.

BRIEF DESCRIPTION OF THE DRAWINGS

FIG. 2E is a simplified, rear view of an expandable mammalian bony segment stabilization implant system in an expanded configuration according to various embodiments.

FIG. 2F is a simplified, front view of another expandable mammalian bony segment stabilization implant system in an expanded configuration according to various embodiments.

FIG. 2I is a simplified, left view of an expandable mammalian bony segment stabilization implant system in an unexpanded configuration according to various embodiments.

DETAILED DESCRIPTION

Figure 1B:
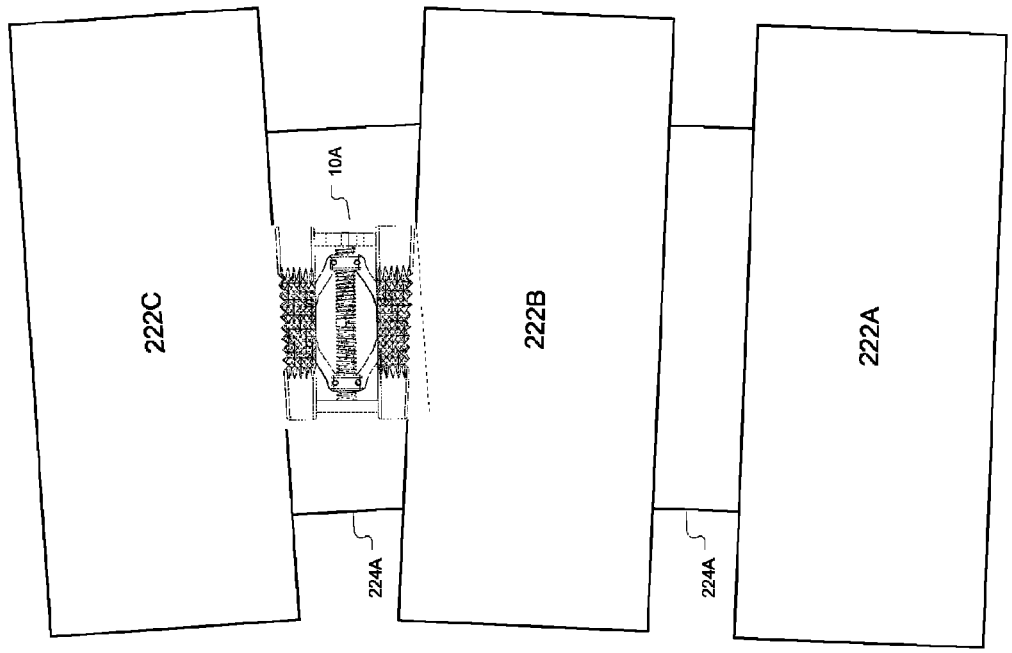
FIG. 1B is a simplified diagram of mammalian bony segment stabilization architecture with an implant system in an expanded configuration according to various embodiments.
Figure 1A:
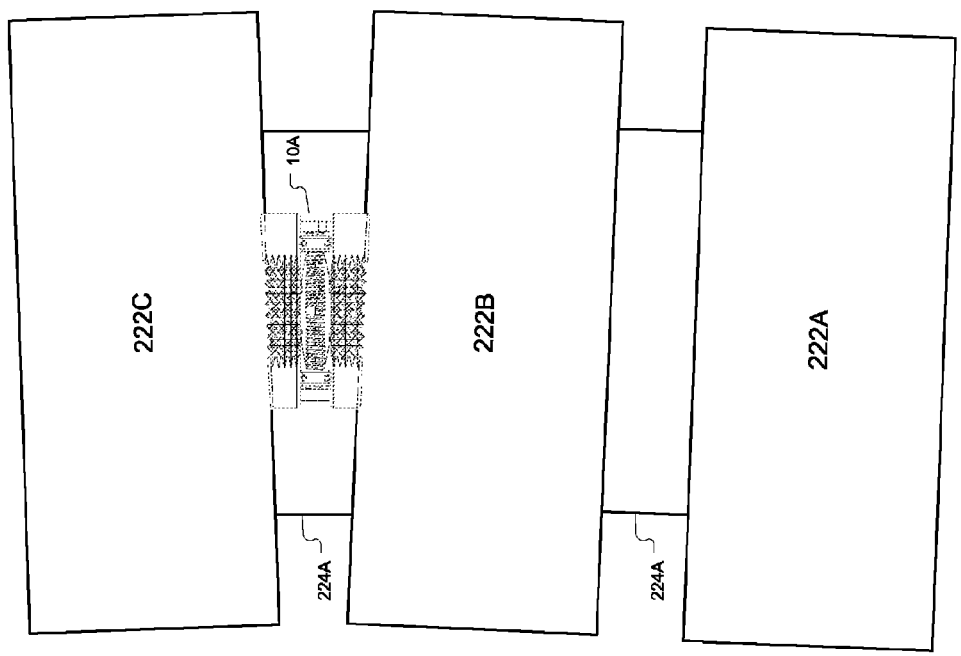
FIG. 1A is a simplified diagram of mammalian bony segment stabilization architecture with an implant system in an unexpanded configuration according to various embodiments.

FIG. 1A is a simplified diagram of mammalian bony segment stabilization architecture 220A with an implant system 10A in an unexpanded configuration according to various embodiments. The architecture 220A includes at least one implant system 10A inserted between bony regions 222C, 222B. In an embodiment the implant system 10A may be inserted any axial direction between two bony regions 222C, 222B, 222A including laterally, anteriorly, and posteriorly. In another embodiment one or more implant systems 10A, 10B (FIG. 2F) may be inserted posteriorally between any two bony regions 222A, 222B, 222C. Further one or more implant systems 10A, 10B, 10C may be inserted laterally and one or more implant systems 10A, 10B, 10C may be inserted posteriorally between any two bony regions 222A, 222B, 222C. Additionally the implant systems 10A, 10B may be inserted at any angle between two bony regions 222A, 222B, 222C as a function of anatomy adjacent the respective two bony regions 222A, 222B, 222C.

FIG. 1B is a simplified diagram of mammalian bony segment stabilization architecture 220B with an implant system 10A in an expanded configuration according to various embodiments. In an embodiment one or more implant systems 10A may be inserted between two bony segments 222A, 222B, 222C with a reduced height profile between an upper implant 20A and a lower implant 20B. The implant system 10A profile or distance between an upper implant 20A and a lower implant 20B may be expanded via an expansion mechanism 100 (FIG. 2K).

In an embodiment the distance between the upper bony segment interface body (BSIB) 20A front edge 22A and lower bony segment interface body (BSIB) 20B front edge 22B (front distance) and the upper BSIB 20A rear edge 27A and lower BSIB 20B rear edge 27B (rear distance) may be simultaneously adjusted via a rear ratcheting mechanism 90 (FIG. 2E). In another embodiment the front distance and the rear distance may be simultaneously adjusted via a rear ratcheting mechanism 70 (FIG. 2F). In a further embodiment the front distance may be adjusted via a front ratcheting mechanism 70 (FIG. 2F) and the rear distance may be independently adjusted via a rear ratcheting mechanism 90 (FIG. 2E).

In an embodiment an implant system 10A, 10B may be inserted between two bony segments 222A, 222B, 222C in a substantially unexpanded state (FIG. 1A) and then expanded via the rear mechanism 90 (FIG. 2E), the front mechanism 70 (FIG. 2F) or a combination of both mechanisms 70, 90. The expanded implant system 10A, 10B may increase the separation between two, adjacent bony segments 222A, 222B, 222C. As a function of the mechanisms 70, 90 operation and implant system 10A, 10B placement (between bony segments 222A, 222B, 222C) the expanded implant system 10A, 10B may increase the anterior distance between adjacent bony segments 222A, 222B, 222C, the superior distance between adjacent bony segments 222A, 222B, 222C, or a combination of both separately or simultaneously. Further as a function of the mechanisms 70, 90 operation and implant system 10A, 10B placement (between bony segments 222A, 222B, 222C) the expanded implant system 10A, 10B may increase a first lateral distance between adjacent bony segments 222A, 222B, 222C, and a second, opposite lateral distance between adjacent bony segments 222A, 222B, 222C, or a combination of both separately or simultaneously.

In an embodiment one or more implant systems 10A, 10B may be inserted via a first axial direction between a first, adjacent bony segments 222A, 222B, 222C and one or more implant systems 10A, 10B may be inserted via a second axial direction between a second, adjacent bony segments 222A, 222B, 222C where the first axial direction and the second axial direction may be the same or different. Further an implant system 10A, 10B may be inserted in a substantially unexpanded state (FIG. 1A) or partially expanded state (FIG. 1B). The implant system 10A, 10B front distance or rear distance may be increased separately or simultaneously via the rear ratcheting mechanism 90 or the front ratcheting mechanism 70 as desired or required. In an embodiment the front distance and rear distance may be equal or unequal as a function of the implant system 10A, 10B placement between two adjacent bony segments 222A, 222B, 222C. In an embodiment the front distance or separation between BSIB 20A, 20B may be less than the rear distance to promote lordosis between the adjacent bony segments 222A, 222B, 222C.

In an embodiment the adjacent bony segments 222A, 222B, 222C may be adjacent vertebra including the sacrum with a disc 224A between adjacent vertebra. The disc 224A may include an annulus and a disc nucleus pulposus. In an embodiment an implant system 10A, 10B may be inserted into a disc nucleus via an opening in the annulus (annulotomy) to increase the distance between adjacent vertebra 222A, 222B, 222C. An implant system 10A, 10B may be expanded to increase a distance between adjacent vertebra 222A, 222B, 222C (uniformly, front, or rear distance) of the implant system 10A, 10B to effectively decompress an intervertebral disc 224A.

Figure 2A:
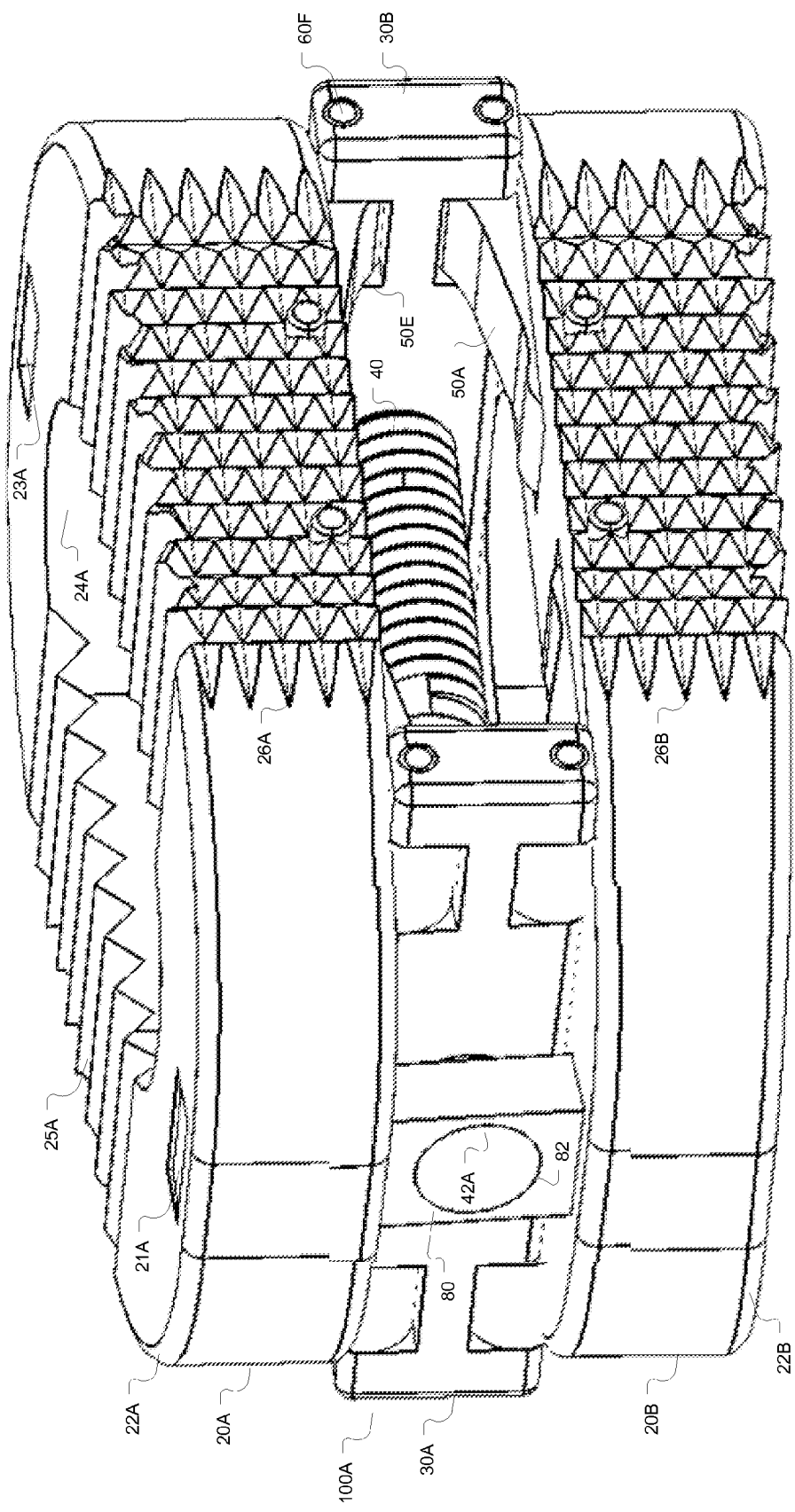
FIG. 2A is a simplified, isometric view of an expandable mammalian bony segment stabilization implant system in a substantially unexpanded configuration according to various embodiments.

FIG. 2A is a simplified, isometric view of an expandable mammalian bony segment stabilization implant system 10A in a substantially unexpanded configuration according to various embodiments. The implant system 10A may include an upper bony segment interface body ("BSIB") 20A, a lower bony segment interface body ("BSIB") 20B, and an expansion mechanism 100A. The expansion mechanism 100A may be operatively coupled to the upper BSIB 20A and the lower BSIB 20B to expand or change the distance between the upper BSIB 20A and the lower BSIB 20B.

The upper BSIB 20A may be shaped to engage a portion of a first bony segment 222A, 222B, 222C and the lower BSIB 20B may be shaped to engage a portion of a second bony segment 222A, 222B, 222C adjacent the first bony segment. In an embodiment the upper BSIB 20A may be substantially rectangular with rounded corners or elliptical in shape and include a sloped front edge 22A. The upper BSIB 20A may also include a large central fenestration 24A where the fenestration 24A may also be substantially rectangular with rounded corners or elliptical in shape. The upper BSIB 20A upper surface may include a plurality of teeth 25A configured to engage a surface of the first bony segment (including an endplate of a vertebral body). The teeth 25A may be racked or angled to the BSIB 20A rear fenestration 23A to limit or prevent slippage of the upper BSIB 20A against the first bony segment. The upper BSIB 20A may include side wall protrusions 26A to engage anatomy (such as disc 224A) adjacent or part of the first bony segment. As shown in FIG. 2A the side wall protrusions may have triangular or pyramid shape.

In an embodiment the lower BSIB 20B may also be substantially rectangular with rounded corners or elliptical in shape and a sloped front edge 22B. The lower BSIB 20B may also include a large central fenestration 24B where the fenestration 24B may also be substantially rectangular with rounded corners or elliptical in shape. The lower BSIB 20B lower surface may include a plurality of teeth 25B (FIG. 2D) to engage a surface of the second bony segment. The teeth 25B may be racked or angled (to the rear in an embodiment) to limit or prevent slippage of the lower BSIB 20B against the second bony segment. The lower BSIB 20B may include side wall protrusions 26B to engage anatomy (such as disc 224A) adjacent or part of the second bony segment. As shown in FIG. 2A the side wall protrusions may have triangular or pyramid shape.

The upper BSIB 20A may also include a first extension fenestration 21A and a second extension fenestration 23A. The first extension fenestration 21A may be shaped to provide a slot for an expansion mechanism arm or extension 80 (FIG. 2A) 70A (FIG. 2F). The second extension fenestration 23A may be shaped to provide a slot for a rear ratchet mechanism 90 arm 90A or an expansion mechanism arm or extension 80 (FIG. 2A). In an embodiment the first and second fenestrations 21A, 23A may be rectangular, square, or elliptical in shape as a function of the corresponding extension 80, and ratcheting mechanism 70 or 90 respectively. Similarly the lower BSIB 20B may also include a first extension fenestration 21B and a second extension fenestration 23B (FIG. 2J). The first extension fenestration 21B may be shaped to provide a slot for an expansion mechanism arm or extension 70A. The second extension fenestration 23B may be shaped to provide a slot for an ratcheting mechanism 90 arm 90A (FIG. 2E) or expansion mechanism arm or extension 80 (FIG. 2A). In an embodiment the first and second fenestrations 21B, 23B may be rectangular, square, or elliptical in shape as a function of the corresponding extension 90A, 80, and extension 70 respectively.

Figure 2B:
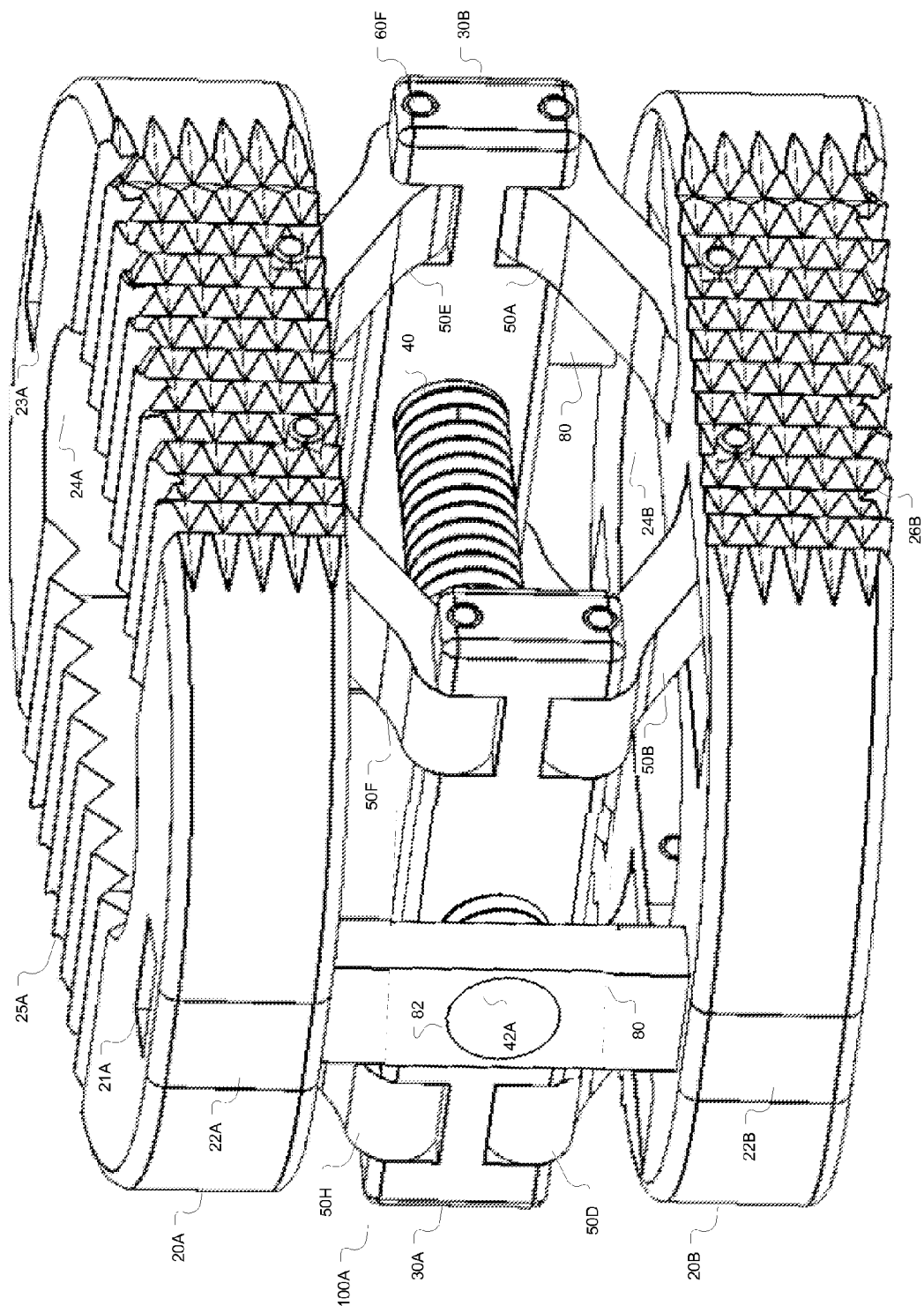
FIG. 2B is a simplified, isometric view of an expandable mammalian bony segment stabilization implant system in an expanded configuration according to various embodiments.
Figure 2C:
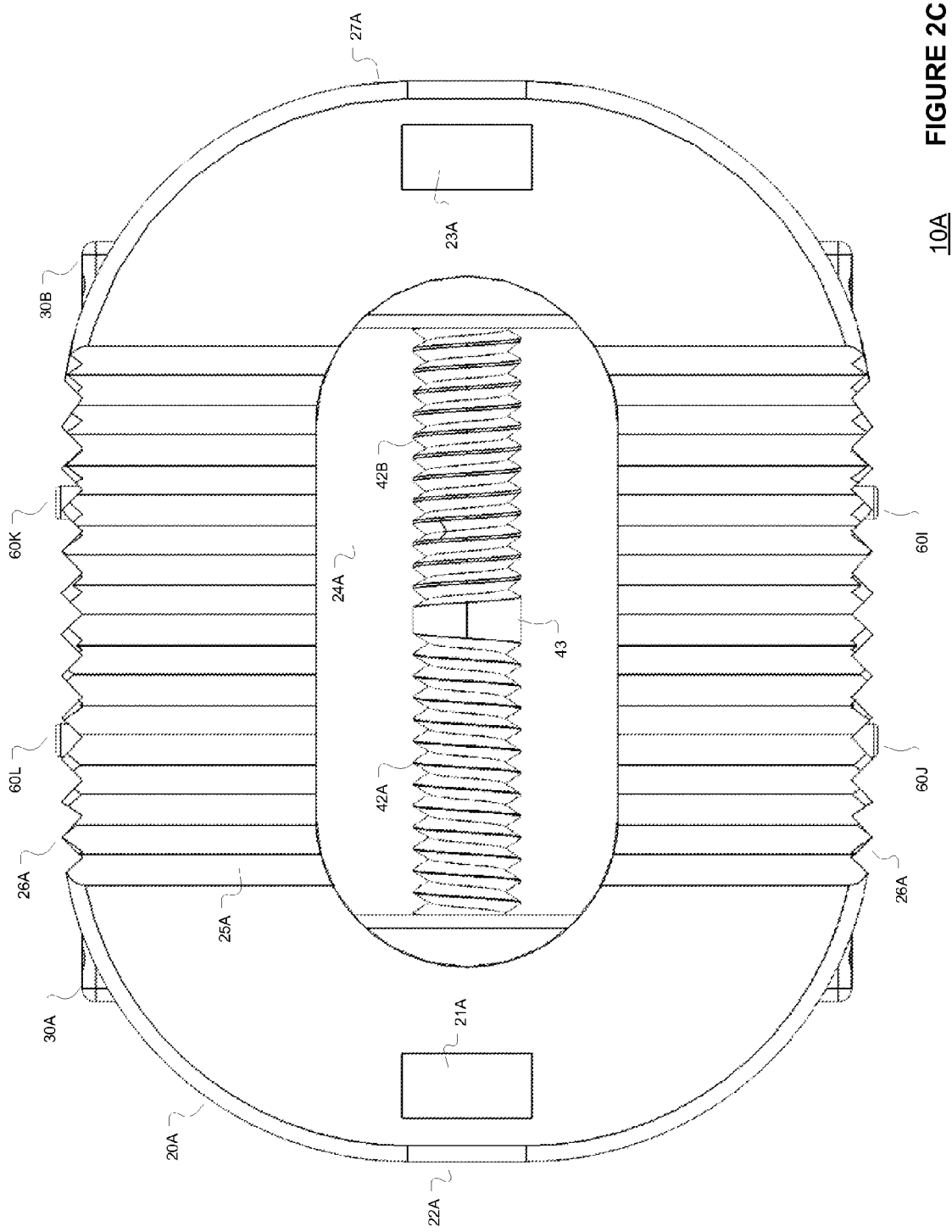
FIG. 2C is a simplified, top view of an expandable mammalian bony segment stabilization implant system in an expanded configuration according to various embodiments.
Figure 2D:
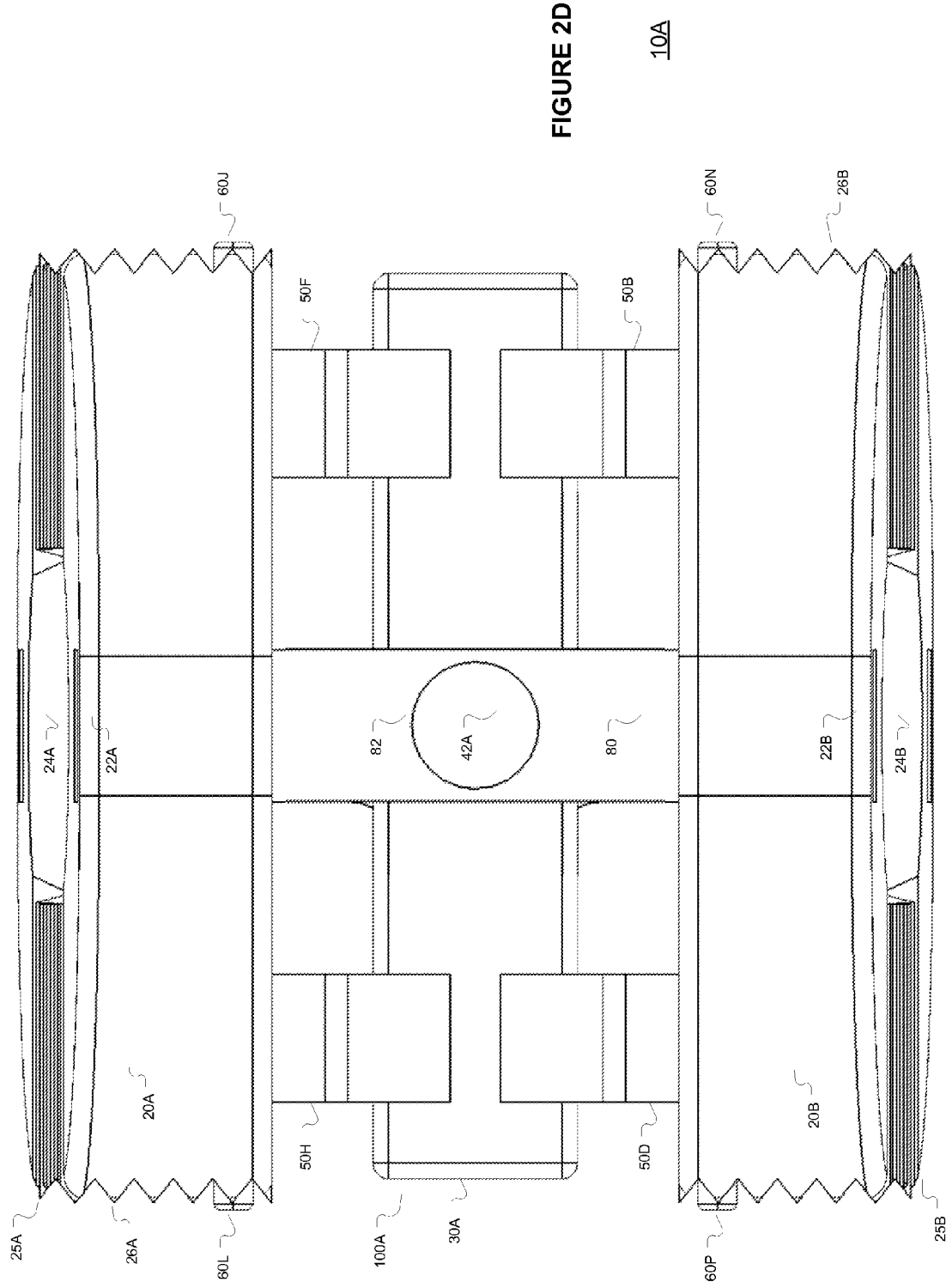
FIG. 2D is a simplified, front view of an expandable mammalian bony segment stabilization implant system in an expanded configuration according to various embodiments.
Figure 2G:
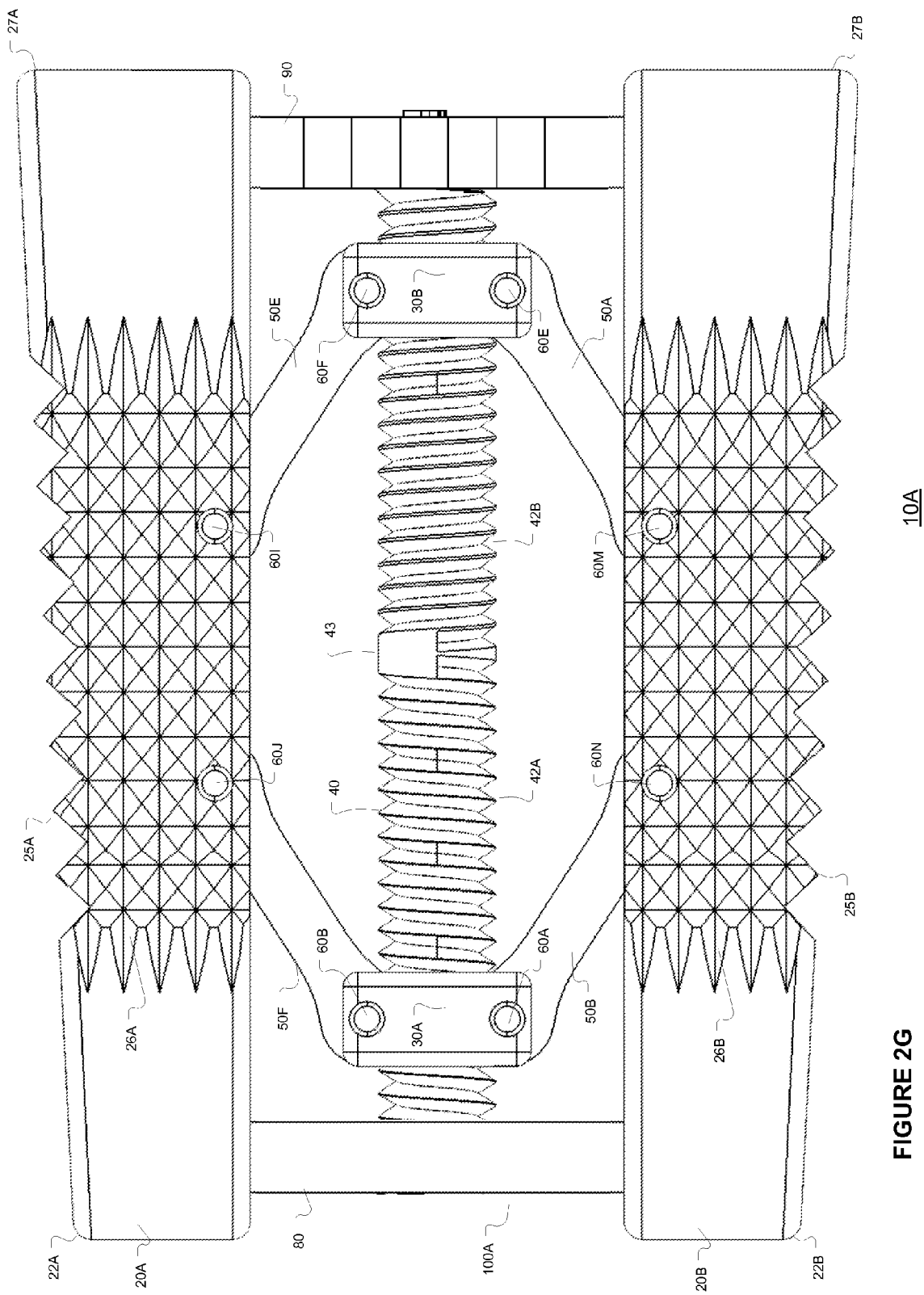
FIG. 2G is a simplified, right view of an expandable mammalian bony segment stabilization implant system in an expanded configuration according to various embodiments.
Figure 2H:
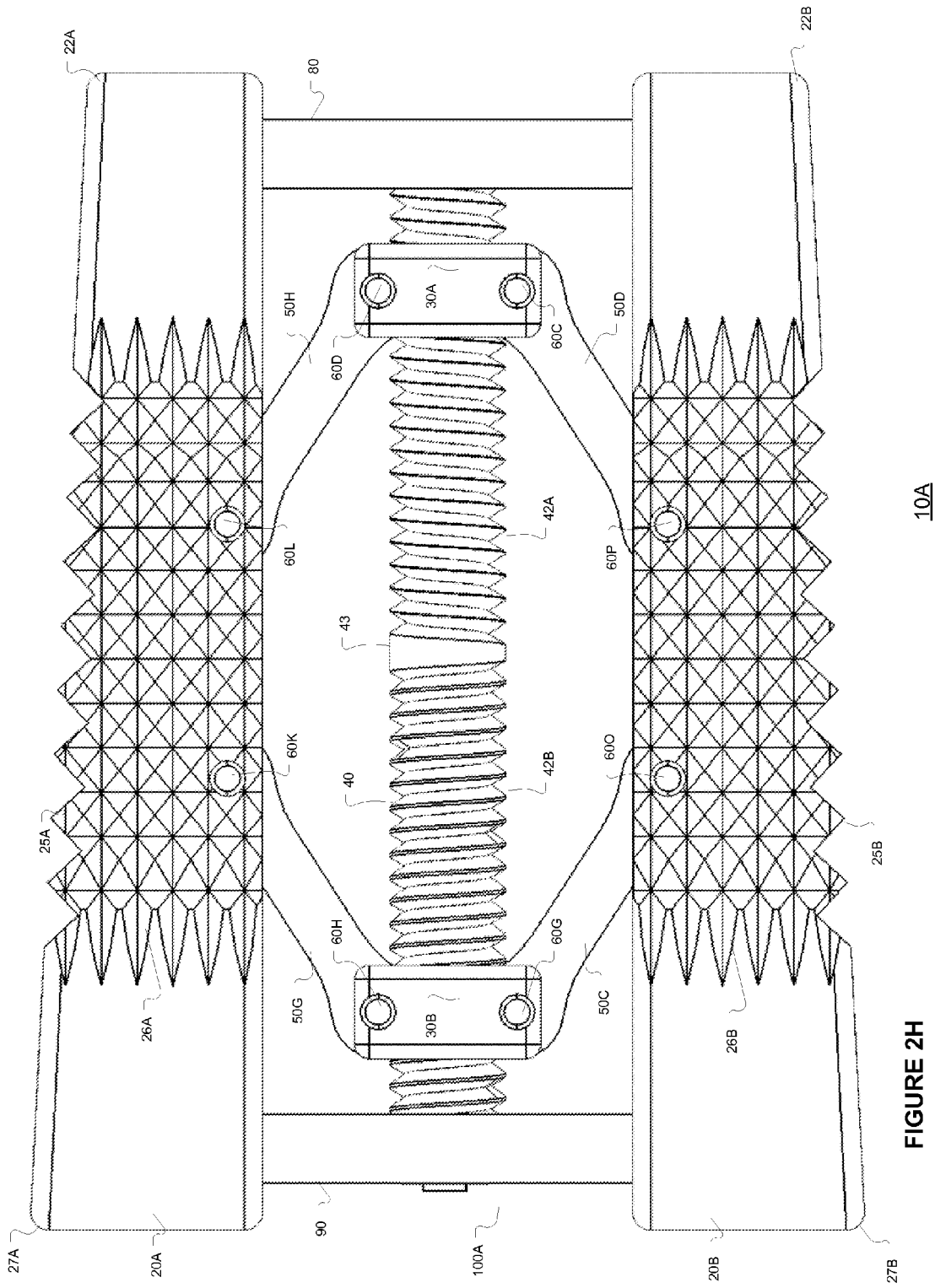
FIG. 2H is a simplified, left view of an expandable mammalian bony segment stabilization implant system in an expanded configuration according to various embodiments.
Figure 21:
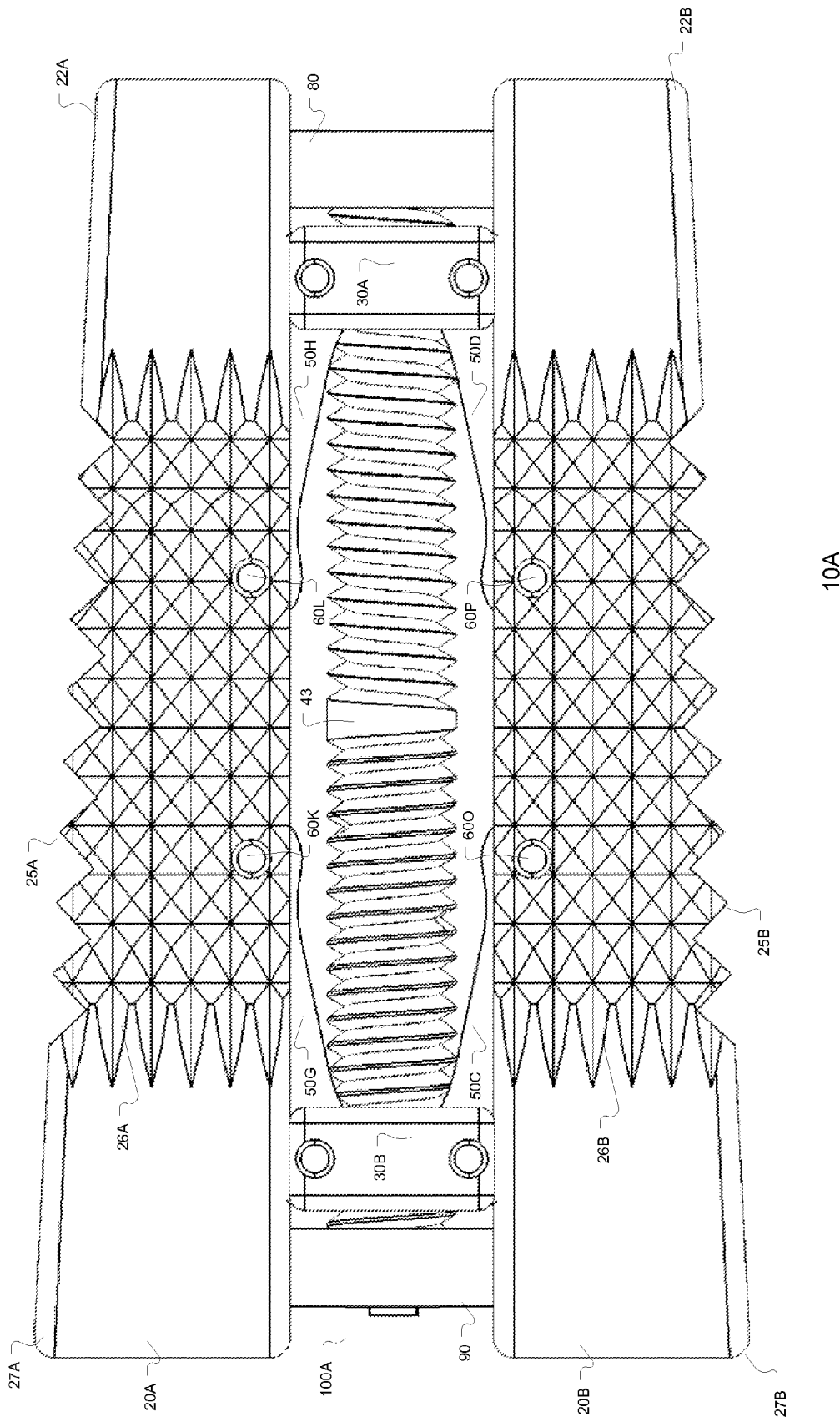
Figure 2J:
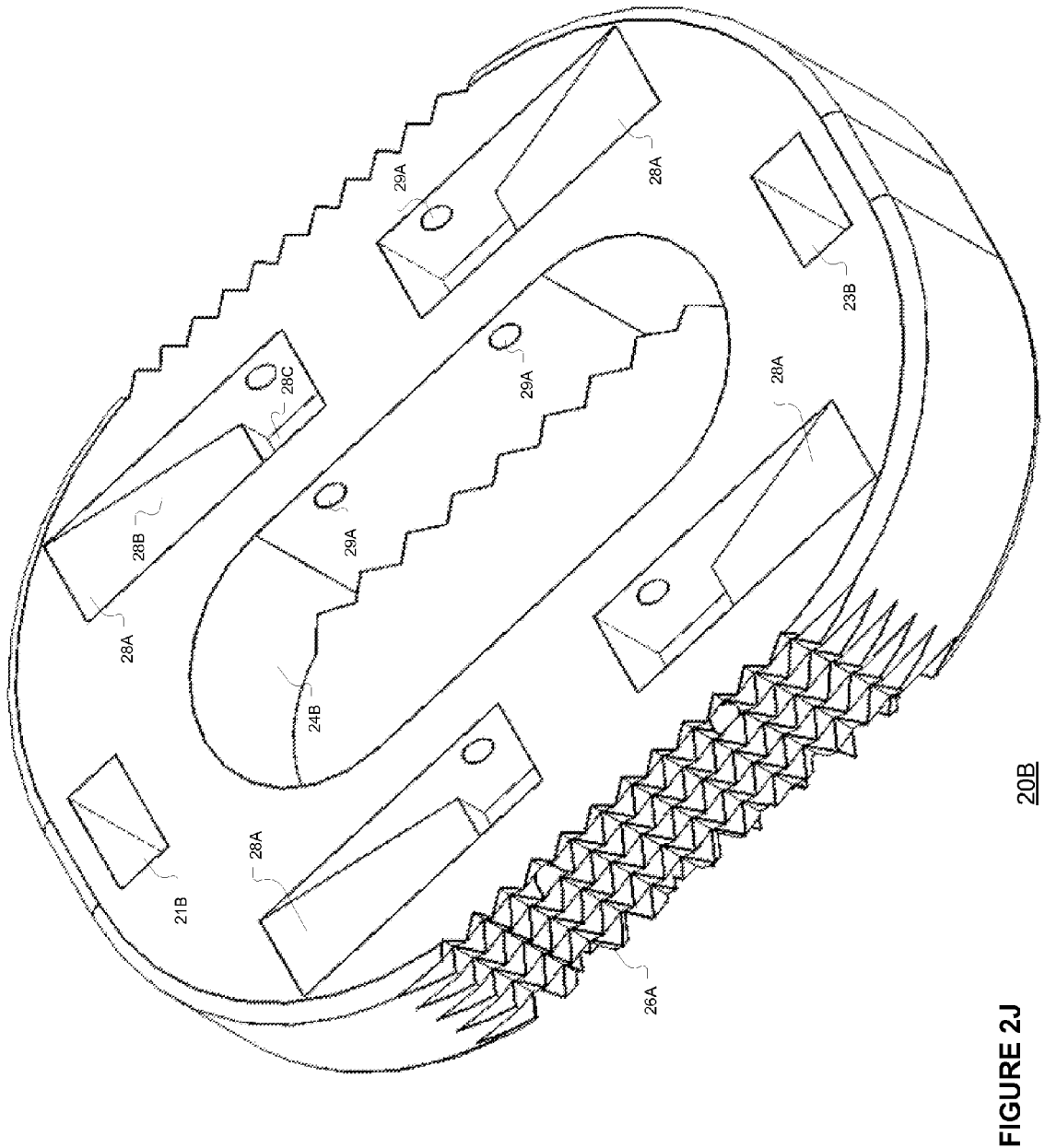
FIG. 2J is a simplified, isometric view of a mammalian bony segment stabilization implant system lower bony segment interface body according to various embodiments.
Figure 2K:
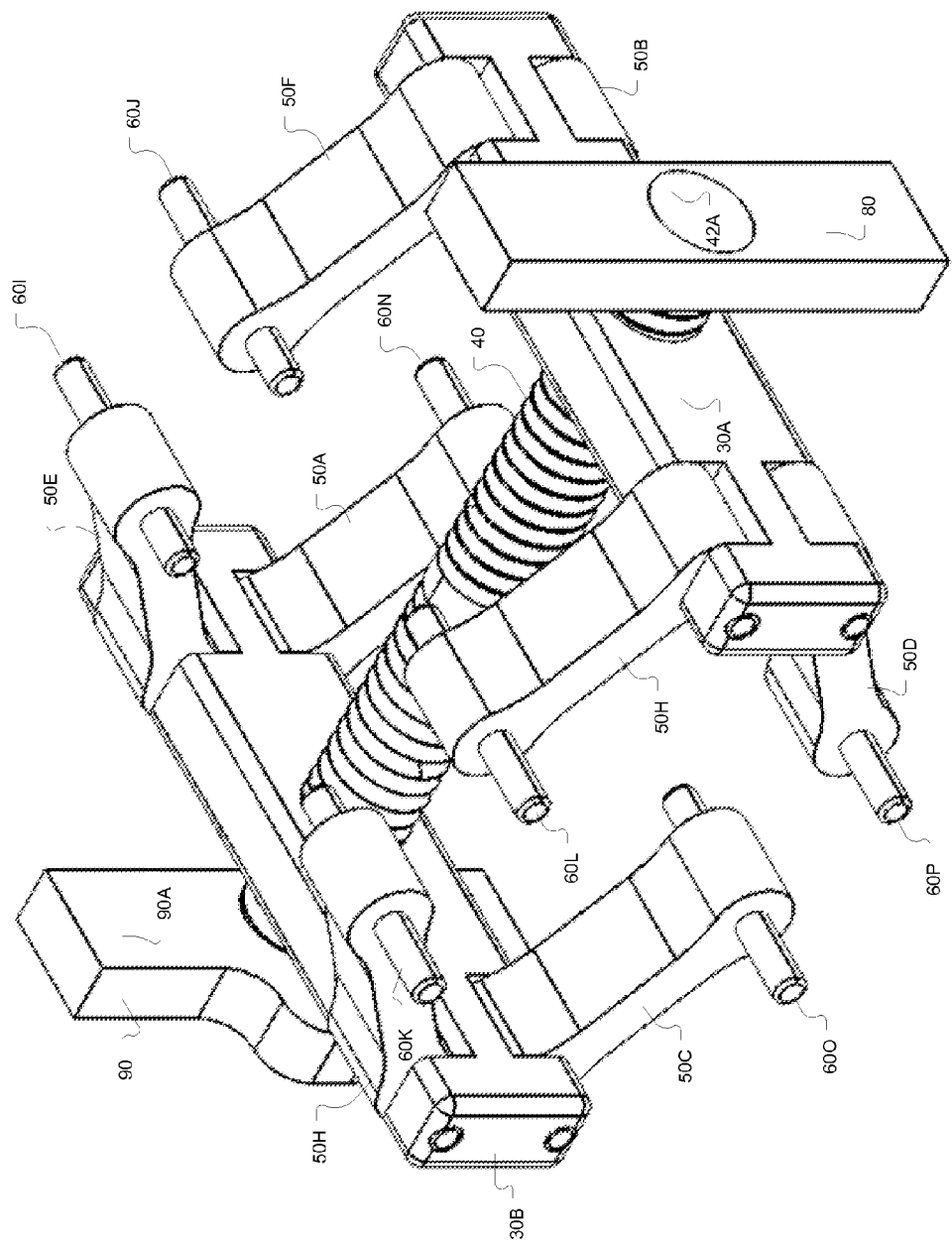
FIG. 2K is a simplified, isometric view of a mammalian bony segment stabilization expansion mechanism according to various embodiments.

As shown in FIG. 2B, FIG. 2G, and 2H, the upper BSIB 20A may be pivotally coupled to the extension mechanism 100A, 100B via a plurality of links 50F, 50E, 50G, 50H. The plurality of links 50F, 50E, 50G, 50H may be pivotally coupled to the upper BSIB 20A via pins 60J, 60I, 60K, 60L, respectively placed in BSIB pin fenestrations 29A (FIG. 2J). Similarly as shown in FIG. 2B, FIG. 2G, and 2H, the lower BSIB 20B may be pivotally coupled to the extension mechanism 100A, 100B via a plurality of links 50B, 50A, 50C, 50D. The plurality of links 50B, 50A, 50C, 50D may be pivotally coupled to the lower BSIB 20B via pins 60N, 60M, 60O, 60P, respectively placed in BSIB pin fenestrations 29A (FIG. 2J).

FIG. 2B is a simplified, isometric view of an expandable mammalian bony segment stabilization implant system 10A in an expanded configuration according to various embodiments. As shown in FIG. 2B the distance between the upper BSIB 20A and the lower BSIB 20B has increased, increasing the overall height of the implant system 10A. As also shown in FIG. 2B the links 50F, 50E, 50G, 50H coupled to the upper BSIB 20A via pins 60J, 60I, 60K, 60L, respectively have pivoted vertically relative to their position shown in FIG. 2A. Similarly, the links 50B, 50A, 50C, 50D coupled to the lower BSIB 20B via pins 60N, 60M, 60O, 60P, respectively have pivoted vertically relative to their position shown in FIG. 2A.

FIG. 2C is a simplified, top view of an expandable mammalian bony segment stabilization implant system 10A in an expanded configuration according to various embodiments. FIG. 2C shows the pins 60J, 60I, 60K, 60L that pivotally couple the links 50F, 50E, 50G, 50H to the upper BSIB 20. FIG. 2C also shows a ratchet screw 40 of an extension mechanism 100A, 100B. The extension mechanism 100A, 100B screw may have a first thread pitch 42A that may drive into a front screw nut and link pivot connection arm 30A. The extension mechanism 100A, 100B screw 40 may have a second thread pitch 42B that may drive into a back screw nut and link pivot connection arm 30B. The second thread pitch 42B may be opposite the pitch of the first thread pitch 42A where the first and second thread sections 42A and 42B are linked by section 43.

In this embodiment when the screw 40 is rotated by the ratcheting mechanism 70 (FIG. 2F) or 90 (FIG. 2E), the respective pivot arms 30A, 30B may be moved simultaneously either toward each other or away from each other. In another embodiment the first screw section 42A may not be rotatably linked to the second screw section 42B via the section 43. In this embodiment the front ratcheting mechanism 70 may separately enable the rotation of the screw section 42A of the screw 40 and separately move the front screw nut and link pivot connection arm 30A relative to the rear screw nut and link pivot connection arm 30B. Similarly, the second screw section 42B may not be rotatably linked to the first screw section 42A via the section 43. In this embodiment the rear ratcheting mechanism 90 may separately enable the rotation of the screw section 42B of the screw 40 and separately move the rear screw nut and link pivot connection arm 30B relative to the front screw nut and link pivot connection arm 30A.

FIG. 2D is a simplified, front view of an expandable mammalian bony segment stabilization implant system 10A in an expanded configuration according to various embodiments. As shown in FIG. 2D the expansion mechanism 100A may include an end cap and extension 80 in front of the arm 30A. The end cap and extension 80 may an opening 82 for the screw 40 second section 42A end. The end cap and extension 80 screw opening 82 may enable the screw 40 second section 42A to rotate within the end cap and extension 80 so the front screw nut and link pivot connection arm 30A may move inwardly and accordingly the increase the distance between the upper BSIB 20A from the lower BSIB 20B, expanding the front of the implant system 10A when the implant system 10A rear is also expanding. As noted the first screw section 42A thread pitch may be opposite the second section 42B to cause the arms 30A, 30B to either move toward each at the same time or away from each other at the same time.

FIG. 2E is a simplified, rear view of an expandable mammalian bony segment stabilization implant system 10A in an expanded configuration according to various embodiments. As shown in FIG. 2E the implant system 10A may include a rear ratchet mechanism 90. The rear ratchet mechanism 90 may include a cover and extension 90A, a lower pawl 90B, an upper pawl 90C, and a direction level 90D. The screw 40 section 42B end may include a gear 44B having a plurality of teeth and a recessed tool interface 45B.

As shown in FIG. 2E the gear 44B teeth spacing may enable the lower pawl 90B or upper pawl 90C to engage teeth at spaced intervals. The gear 44B may include 16 teeth in an embodiment. The level 90D may be employed to engage the upper pawl 90C and disengage the lower pawl 90B to enable rotation of the screw 40 section 42B in a first counter-clockwise direction. Similarly, the level 90D may be employed to engage the lower pawl 90B and disengage the upper pawl 90C to enable rotation of the screw 40 section 42B in a second clockwise direction. In an embodiment, rotation of the screw 40 section 42B in a clockwise direction may cause the rear screw nut and link pivot connection arm 30B to move inward and accordingly increase the distance between the upper BSIB 20A from the lower BSIB 20B, expanding at least the rear of the implant system 10A. In an embodiment rotation of the screw 40 second screw section 42B may cause the first screw section 42A to rotate simultaneously. As shown in FIG. 2D, the implant system 10A front may include an end cap and extension 80 with an opening 82 that enables the screw 40 first section 42A to rotate freely while the second section 42B is rotated via the tool recess 45B.

FIG. 2F is a simplified, front view of an expandable mammalian bony segment stabilization implant system 10B in an expanded configuration according to various embodiments. As shown in FIG. 2F the implant system 10A may include a front ratchet mechanism 70. The front ratchet mechanism 70 may include a cover and extension 70A, lower pawl 70B, upper pawl 70C, and direction level 70D. The screw 40 section 42A end may include a gear 44A having a plurality of teeth and a recessed tool interface 45A. As shown in FIG. 2F the gear 44A teeth spacing may enable the lower pawl 70B or upper pawl 70C to engage teeth at spaced intervals. The gear 44A may include 16 teeth in an embodiment. The level 70D may be employed to engage the upper pawl 70C and disengage the lower pawl 70B to enable rotation of the screw 40 section 42A in a first counter-clockwise direction. Similarly, the level 70D may be employed to engage the lower pawl 70B and disengage the upper pawl 70C to enable rotation of the screw 40 section 42A in a second clockwise direction. In an embodiment, rotation of the screw 40 section 42A in a counter-clockwise direction may cause the front screw nut and link pivot connection arm 30A to move inward and accordingly the distance between the upper BSIB 20A to increase from the lower BSIB 20B, expanding at least the front of the implant system 10A. In the implant system 10B rear may include an end cap and extension 80 with an opening 82 that enables the screw 40 second section 42B to rotate freely while the first section 42A is rotated via the tool recess 45A.

FIG. 2G is a simplified, right view of an expandable mammalian bony segment stabilization implant system 10A in an expanded configuration according to various embodiments. FIG. 2H is a simplified, left view of an expandable mammalian bony segment stabilization implant system 10A in an expanded configuration according to various embodiments. As shown in FIG. 2G and FIG. 2H the implant system 10A upper BSIB 20A may be connected to the expansion mechanism 100 front screw nut and link pivot connection 30A via the link 50G and related pins 60K and 60H, link 50H and related pins 60L and 60D, link 50F and related pins 60J and 60B, and link 50E and related pins 60I and 60F. As shown in FIG. 2G and FIG. 2H the implant system 10A lower BSIB 20B may be connected to the expansion mechanism 100 front screw nut and link pivot connection 30A via the link 50C and related pins 60O and 60G, link 50D and related pins 60P and 60C, link 50B and related pins 60N and 60A, and link 50A and related pins 60M and 60E.

FIG. 2I is a simplified, left view of an expandable mammalian bony segment stabilization implant system 10A in an unexpanded configuration according to various embodiments. As shown in FIG. 2I the upper BSIB 20A and the lower BSIB 20B may rest against the front screw nut and link pivot connection arm 30A and the rear screw nut and link pivot connection arm 30B when the implant system 10A is substantially unexpanded. The end cap and extension 80 may extend into the upper BSIB 20A rear fenestration 23A and the lower BSIB 20B rear fenestration 23B. Similarly the front ratcheting mechanism 70 extension 70A may extend into the upper BSIB 20A front fenestration 21A and the lower BSIB 20B front fenestration 21B. For implant system 10B (shown in FIG. 2F), the rear ratcheting mechanism 90 extension 90A may extend into the upper BSIB 20A rear fenestration 23A and the lower BSIB 20B rear fenestration 23B.

As the implant system 10A expands as shown in FIGS. 2G and 2H the front screw nut and link pivot connection arm 30A and the rear screw nut and link pivot connection arm 30B may move inward to the implant system 10A screw 40 middle section 43 causing the links 50A to 50H to rotate about the pins 60A to 60P and cause the BSIB 20A and BSIB 20B to move apart from the arms 30B, 30A. As noted in an embodiment activation of the rear ratcheting mechanism 90 in a first rotation may cause the entire screw 40, sections 42A and 42B to rotate in the same first direction. In another embodiment, activation of the rear ratcheting mechanism 90 in a first rotation may only cause the adjacent screw 40 rear section 42B to rotate in the same first direction. Similarly in an embodiment activation of the front ratcheting mechanism 70 (FIG. 2F) in a first rotation may cause the entire screw 40, sections 42A (front) and 42B (rear) to rotate in the same first direction. In another embodiment, activation of the front ratcheting mechanism 70 in a first rotation may only cause the adjacent screw 40 front section 42A to rotate in the same first direction.

FIG. 2J is a simplified, isometric view of a mammalian bony segment stabilization implant system 10A, 10B lower BSIB 20B according to various embodiments. As shown in FIG. 2J the BSIB 20B may include a front fenestration 21B, a rear fenestration 22B, and a central, elliptical fenestration 24B. The front and rear fenestrations 21B, 23B may have a shape that mates with the rear ratcheting mechanism 90 extension 90A, the end cap and extension 80, and the front ratcheting mechanism 70 extension 70A. The front and rear fenestrations 21B, 23B may be rectangular in shape in an embodiment. As shown in FIG. 2J the lower BSIB 20B may include fenestrations 29A for pins 60M to 60P where the pins 60M to 60P rotatably couple a link 50A to 50D to the lower BSIB 20B. In an embodiment the lower BSIB 20B may include openings 28A for each link 50A to 50D where the openings 28A are shaped to provide complementary shape for a link 50A to 50D so the link 50A to 50D may be at least partially recessed in the lower BSIB 20B when the implant system 10A, 10B is not fully expanded.

As shown in FIG. 2J a link 50A to 50D accommodating opening 28A may include a slanted recess or ramp 28B and deep section 28C. The deep section 28C may accommodate the curved end portion of a link 50A to 50D and the slanted recess or ramp 28B may accommodate the central arm of a link 50A to 50D. FIG. 2K is a simplified, isometric view of a mammalian bony segment stabilization expansion mechanism 100A according to various embodiments. As shown in FIGS. 2A-2E, 2G-2I the expansion mechanism 100A links 50A to 50H may be rotatably coupled to an upper BSIB 20A and a lower BSIB 20B via the pins 60I to 60P. As shown in FIG. 2K, the expansion mechanism 100A may include a rear ratcheting mechanism 90, a rear end cap and extension 80, front screw nut and link pivot connection arm 30A, rear screw nut and link pivot connection arm 30B, links 50A-50H, pins 60A to 60P, and screw 40. In another embodiment the front end cap and extension 80 may be replaced by a front ratcheting mechanism 70 as shown in FIG. 2F.

In an embodiment the expansion mechanism 100A may include a different ratcheting mechanism 70, 90. The mechanism 100A may include additional links 50A to 50H. In a further embodiment the mechanism may not include end cap and extension 80. In another embodiment the expansion mechanism may only be pivotally coupled to the one of the upper BSIB 20A and the lower BSIB 20B. In the embodiment the expansion mechanism 10A, 10B may only lift one of the two BSIB 20A, 20B relative to the other of the BSIB 20A, 20B. The expansion mechanism 10A, 10B may be fixably coupled the other of the BSIB 20A, 20B.

In an embodiment, the implant system's 10A, 10B unexpanded height between the upper BSIB 20A front edge 22A and the lower BSIB 20B front edge 22BA may range from 5 to 16 mm. In an embodiment, the implant system's 10A, 10B expanded height between the upper BSIB 20A front edge 22A and the lower BSIB 20B front edge 22BA may range from 8 to 30 mm. The implant system's 10A, 10B maximum length between the front 70 and rear 80, 90 may range from 8 to 35 mm. The implant system's 10A, 10B maximum width may range from 6 mm to 25 mm. Each BSIB 20A, 20B central fenestration 24A, 24B may have a length from about 5 to 30 mm and a width from about 3 to 5 mm. Each BSIB 20A, 20B front fenestration 21A, 21B may have a length from about 1 to 6 mm and a width from about 1 to 9 mm in an embodiment. Further, each BSIB 20A, 20B rear fenestration 23A, 23B may have a length from about 1 to 6 mm and a width from about 1 to 9 mm in an embodiment.

In an embodiment the upper BSIB front edges 22A, 22B may have a slope ranging from 10 to 30 degrees with about 25 degrees in an embodiment. Further the top and bottom surfaces 12, 14 may have an effective radius of ranging from 20 to 60 mm and about 40 mm in an embodiment. The implant systems 10A, 10B upper BSIB 20A and lower BSIB 20B teeth 25A, 25B may be spaced about 0.5 to 3.0 mm apart and have a height of about 0.2 to 1.2 mm. The teeth 25A, 25B may have a reverse rack (relative to the upper BSIB 20A front edge 22A and the lower BSIB 20B front edge 22B) of about 46 to 65 degrees (obtuse).

Figure 3A:
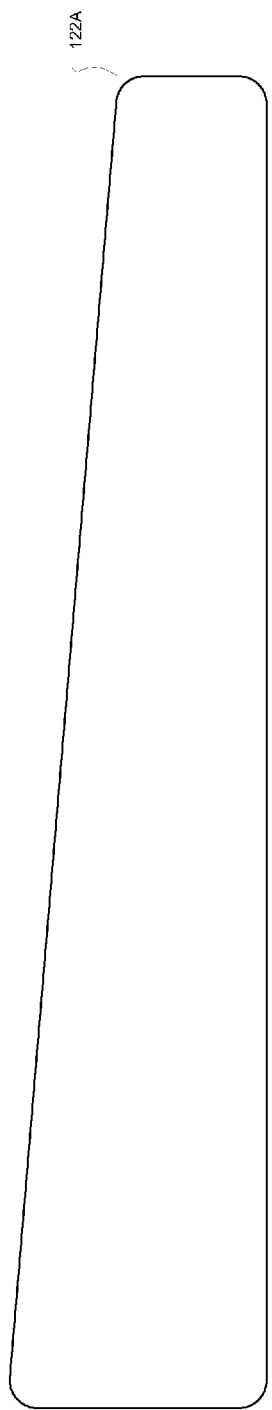
FIG. 3A-3C are simplified, side, profile views of mammalian bony segment stabilization implant system upper bony segment interface bodies according to various embodiments.
Figure 3B:
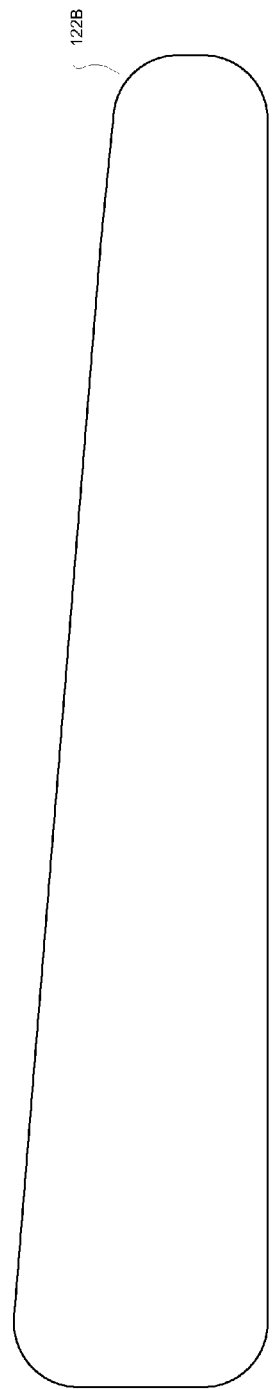
Figure 3C:
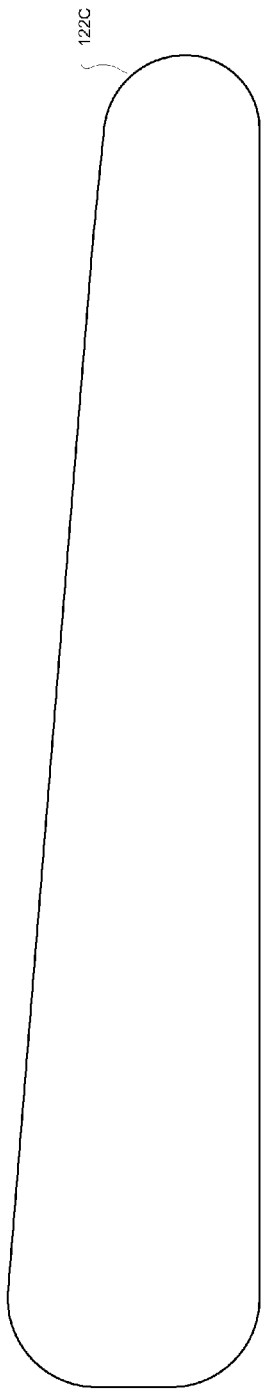

FIG. 3A-3C are simplified, side, profile views of mammalian bony segment stabilization implant system upper bony segment interface bodies 120A, 120B, and 120C according to various embodiments. As shown in these figures a BSIB 120A, 120B, 120C may have a rounded or shaped front edge 122A, 122B, 122C. A lower BSIB 20B of an implant system 10A, 10B may also include rounded or shaped edges 122A, 122B, 122C. An BSIB 120A, 120B, 120C edge 122A, 122B, 122C may have an outer diameter of about 0.5 mm to 4 mm (0.5 mm, 1.2 mm, and 1.5 mm in an embodiment respectively for 122A, 122B, and 122C.) An upper or lower BSIB with additionally rounded or shaped edges 122A, 122B, 122C, 22A, 22B may ease the entry of an implant system 10A, 10B between adjacent bony segments.

In an embodiment the implant system 10A, 10B upper BSIB 20A and lower BSIB 20B may include a radio lucent material including polymers/thermoplastics such as (Polyetheretherketone). The implant system 10A, 10B upper BSIB 20A and lower BSIB 20B may also include radio markers including radio opaque materials including metal alloys such as titanium and tantalum. In an embodiment the implant system 10A, 10B upper BSIB 20A and lower BSIB 20B may include porous openings that may enable bony in-growth in the BSIB 20A, 20B. The BSIB 20A, 20B material may include a bone growth activator or bio-active elements including a calcium based hydroxylapatite or hydroxyapatite. Further the implant system 10A, 10B upper BSIB 20A and lower BSIB 20B surfaces may be coated with a bio-active element or coatings including a hydroxyapatite to encourage bony growth between a bony surface 222A, 222B, 222C and an BSIB 20A, 20B. It is noted that the BSIB 20A, 20B and expansion mechanisms 100A, 100B may be comprised of any biocompatible material including bone, polymers, and metals.

The accompanying drawings that form a part hereof show, by way of illustration and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In the foregoing Detailed Description, various features are grouped together in a single embodiment for the purpose of streamlining the disclosure. This method of disclosure is not to be interpreted to require more features than are expressly recited in each claim. Rather, inventive subject matter may be found in less than all features of a single disclosed embodiment. Thus the following claims are hereby incorporated into the Detailed Description, with each claim standing on its own as a separate embodiment.

Table of Reference Numerals

| | |
|---|---|
| 10A | Expandable Implant system |
| 10B | Expanded Implant system |
| 20A | Upper bony segment interface body |
| 20B | Lower Bony segment interface body |
| 21A | Upper Bony segment interface body Front Extension fenestration |
| 21B | Lower Bony segment interface body Front Extension fenestration |
| 22A | Upper Bony segment interface body Front Edge |
| 22B | Lower Bony segment interface body Front Edge |
| 23A | Upper Bony segment interface body Back Extension fenestration |
| 23B | Lower Bony segment interface body Back Extension fenestration |
| 24A | Upper Bony segment interface body central fenestration |
| 24B | Lower Bony segment interface body central fenestration |
| 25A | Upper Bony segment interface body teeth |
| 25B | Lower Bony segment interface body teeth |
| 26A | Upper Bony segment interface body side wall protrusions |
| 26B | Lower Bony segment interface body side wall protrusions |
| 27A | Upper Bony segment interface body Back Edge |
| 27B | Lower Bony segment interface body Back Edge |
| 28A | Bony segment interface body cavity for pin arm |
| 28B | Bony segment interface body cavity sloped ram |
| 28C | Bony segment interface body cavity bottom well |
| 29A | Bony segment interface body pin fenestration |
| 30A | Front screw nut and link pivot connection arm |
| 30B | Back screw nut and link pivot connection arm |
| 40 | Ratchet screw |
| 42A | First Screw thread pattern |
| 42B | Second Screw thread pattern |
| 43 | Screw thread center |
| 44A | Front Screw ratchet teeth |
| 45A | Front Screw hex tool interface |
| 44B | Rear Screw ratchet teeth |
| 45B | Rear Screw hex tool interface |
| 50A | Link, lower, right, back |
| 50B | Link, lower, right, front |
| 50C | Link, lower, left, back |
| 50D | Link, lower, left, front |
| 50E | Link, upper, right, back |
| 50F | Link, upper, right, front |
| 50G | Link, upper, left, back |
| 50H | Link, upper, left, front |
| 60A | Pin coupling link to Front screw nut lower, right |
| 60B | Pin coupling link to Front screw nut upper, right |
| 60C | Pin coupling link to Front screw nut lower, left |
| 60D | Pin coupling link to Front screw nut upper, left |

-continued

Table of Reference Numerals

| | |
|---|---|
| 60E | Pin coupling link to Back screw nut lower, right |
| 60F | Pin coupling link to Back screw nut upper, right |
| 60G | Pin coupling link to Back screw nut lower, left |
| 60H | Pin coupling link to Back screw nut upper, left |
| 60I | Pin coupling link to Upper Bony segment interface body back, right |
| 60J | Pin coupling link to Upper Bony segment interface body front, right |
| 60K | Pin coupling link to Upper Bony segment interface body back, left |
| 60L | Pin coupling link to Upper Bony segment interface body front, left |
| 60M | Pin coupling link to Lower Bony segment interface body back, right |
| 60N | Pin coupling link to Lower Bony segment interface body front, right |
| 60O | Pin coupling link to Lower Bony segment interface body back, left |
| 60P | Pin coupling link to Lower Bony segment interface body front, left |
| 70 | Front Ratchet Mechanism |
| 70A | Front Ratchet Mechanism Cover and extension |
| 70B | Front Ratchet Mechanism Lower Pawl |
| 70C | Front Ratchet Mechanism Upper Pawl |
| 70D | Front Ratchet Mechanism Direction Lever |
| 80 | End Cap and extension |
| 82 | End Cap screw end opening |
| 90 | Rear Ratchet Mechanism |
| 90A | Rear Ratchet Mechanism Cover and extension |
| 90B | Rear Ratchet Mechanism Lower Pawl |
| 90C | Rear Ratchet Mechanism Upper Pawl |
| 90D | Rear Ratchet Mechanism Direction Lever |
| 100A | Expansion Mechanism |
| 100B | Expansion Mechanism |

What is claimed is:

1. A horizontally elongate implant system for stabilizing a bony segment pair, the horizontally elongate implant system including:

a lower bony segment interface body ("BSIB") for engaging a first of the bony segment pair, the lower BSIB having a long horizontal axis and including a front, a top, a first side, a second side, a bottom, and a rear, the BSIB comprised substantially of a non-metallic material;

a upper bony segment interface body ("BSIB") for engaging the other of the bony segment pair, the upper BSIB physically separate from the lower BSIB, having a long horizontal axis and including a front, a top, a first side, a second side, a bottom, and a rear, the BSIB comprised substantially of a non-metallic material; and an expansion mechanism, the expansion mechanism pivotably coupled to one of the lower BSIB and the upper BSIB via a plurality of connection points, the expansion mechanism including at least one ratcheting mechanism, the ratcheting mechanism when activated increasing at least the distance between one of the lower BSIB front and the upper BSIB front and the lower BSIB rear and the upper BSIB rear, the lower BSIB and the upper BSIB each including a central fenestration extending from the top to the bottom, and the lower BSIB and the upper BSIB each include a shaped fenestration extending from the top to the bottom and located between the central fenestration and BSIB front and the expansion mechanism ratcheting mechanism includes an upper and lower extension arm, the upper extension arm complementary shaped to extend into the upper BSIB shaped fenestration and not substantially rotate within the upper BSIB shaped fenestration and the lower extension arm complementary shaped to extend into the lower BSIB shaped fenestration and not substantially rotate within the lower BSIB shaped fenestration.

2. The horizontally elongate implant system for stabilizing a bony segment pair of claim 1, wherein the lower BSIB and upper BSIB are comprised substantially of polyetheretherketone.

3. The horizontally elongate implant system for stabilizing a bony segment pair of claim 2, the lower BSIB and the upper BSIB including a bone growth material.

4. The horizontally elongate implant system for stabilizing a bony segment pair of claim 3, wherein the bone growth material includes hydroxyapatite.

5. The horizontally elongate implant system for stabilizing a bony segment pair of claim 1, wherein the lower BSIB and the upper BSIB tops include a plurality of teeth oriented traverse to the long horizontal axis and inclined to each BSIB rear.

6. The horizontally elongate implant system for stabilizing a bony segment pair of claim 5, wherein the lower BSIB and the upper BSIB first side and second side include a plurality of protrusions extending traverse to each BSIB long horizontal axis.

7. The horizontally elongate implant system for stabilizing a bony segment pair of claim 1, wherein the bony segment pair is a first vertebra immediately adjacent to a second vertebra.

8. The horizontally elongate implant system for stabilizing a bony segment pair of claim 1, wherein the lower BSIB and the upper BSIB each include a second shaped fenestration extending from the top to the bottom and located between the central fenestration and BSIB rear and the expansion mechanism includes an end cap with an upper and lower extension arm, the end cap upper extension arm complementary shaped to extend into the upper BSIB second shaped fenestration and not substantially rotate within the upper BSIB second shaped fenestration and the end cap lower extension arm complementary shaped to extend into the lower BSIB second shaped fenestration and not substantially rotate within the lower BSIB second shaped fenestration.

9. The horizontally elongate implant system for stabilizing a bony segment pair of claim 8, wherein the ratcheting mechanism when activated increases the distance between the lower BSIB front and the upper BSIB front and the lower BSIB rear and the upper BSIB rear substantially the same distance.

10. The horizontally elongate implant system for stabilizing a bony segment pair of claim 9, wherein the expansion mechanism includes a central screw coupled to the ratcheting mechanism and operatively coupled to a plurality of links, the plurality of links coupled to one of the lower BSIB and the upper BSIB via a plurality of connection points.

11. The horizontally elongate implant system for stabilizing a bony segment pair of claim 8, wherein the ratcheting mechanism when activated increases the distance between the lower BSIB front and the upper BSIB front, the expansion mechanism further including a second ratcheting mechanism that when activated increases the distance between the lower BSIB rear and the upper BSIB rear, wherein the ratcheting mechanism and a second ratcheting mechanism operate independently.

12. A horizontally elongate implant system for stabilizing a bony segment pair, the horizontally elongate implant system including:
  a lower bony segment interface body ("BSIB") for engaging a first of the bony segment pair, the lower BSIB having a long horizontal axis and including a front, a top, a first side, a second side, a bottom, and a rear, the BSIB comprised substantially of a non-metallic material;
  an upper body segment interface body ("BSIB") for engaging the other of the bony segment pair, the upper BSIB physically separate from the lower BSIB, having a long horizontal axis and including a front, a top, a first side, a second side, a bottom, and a rear, the BSIB comprised substantially of a non-metallic material; and
  an expansion mechanism, the expansion mechanism pivotably coupled to one of the lower BSIB and the upper BSIB via a plurality of connection points, the expansion mechanism including at least one ratcheting mechanism, the ratcheting mechanism when activated increasing at least the distance between one of the lower BSIB front and the upper BSIB front and the lower BSIB rear and the upper BSIB rear,
  wherein the expansion mechanism is pivotably coupled to lower BSIB and the upper BSIB via a plurality of connection points, the expansion mechanism including at least one ratcheting mechanism, the ratcheting mechanism when activated increasing at least the distance between one of the lower BSIB front and the upper BSIB front and the lower BSIB rear and the upper BSIB rear, the expansion mechanism includes a central screw coupled to the ratcheting mechanism and operatively coupled to a first plurality of links and a second plurality of links, the first plurality of links coupled to one of the lower BSIB and the upper BSIB via a plurality of connection points and the second plurality of links coupled to the other of the lower BSIB and the upper BSIB via a plurality of connection points, and the expansion mechanism further includes a front screw nut and link pivot connection arm, the arm including a nut interfacing with the central screw, wherein the ratcheting mechanism rotates the central screw causing the front screw nut and link pivot connection arm to move in a first direction to expand a portion of the implant system via the links and a second direction to contract a portion of the implant system via the links.

13. The horizontally elongate implant system for stabilizing a bony segment pair of claim 12, wherein the ratcheting mechanism when activated moves the front screw nut and link pivot connection arm and the distance between the lower BSIB front and the upper BSIB front one of increases and decreases.

14. The horizontally elongate implant system for stabilizing a bony segment pair of claim 13, wherein the expansion mechanism further includes a rear screw nut and link pivot connection arm, the arm including a nut interfacing with the central screw, wherein the ratcheting mechanism rotates the central screw causing the rear screw nut and link pivot connection arm to move in a first direction to expand a portion of the implant system via the links and a second direction to contract a portion of the implant system via the links.

15. The horizontally elongate implant system for stabilizing a bony segment pair of claim 14, wherein the ratcheting mechanism when activated moves the rear screw nut and link pivot connection arm and the distance between the lower BSIB rear and the upper BSIB rear one of increases and decreases.

16. The horizontally elongate implant system for stabilizing a bony segment pair of claim 12, wherein the lower BSIB and the upper BSIB each includes a central fenestration extending from the top to the bottom.

17. The horizontally elongate implant system for stabilizing a bony segment pair of claim 16, wherein the bony segment pair is a first vertebra immediately adjacent to a second vertebra.

18. The horizontally elongate implant system for stabilizing a bony segment pair of claim 12, wherein the lower BSIB and the upper BSIB each include a shaped fenestration extending from the top to the bottom and located between the central fenestration and BSIB front and the expansion mechanism ratcheting mechanism includes an upper and lower extension arm, the upper extension arm complementary shaped to extend into the upper BSIB shaped fenestration and not substantially rotate within the upper BSIB shaped fenestration and the lower extension arm complementary shaped to extend into the lower BSIB shaped fenestration and not substantially rotate within the lower BSIB shaped fenestration.

19. The horizontally elongate implant system for stabilizing a bony segment pair of claim 12, wherein the ratcheting mechanism when activated increases the distance between the lower BSIB front and the upper BSIB front, the expansion mechanism further including a second ratcheting mechanism that when activated increases the distance between the lower BSIB rear and the upper BSIB rear, wherein the ratcheting mechanism and a second ratcheting mechanism operate independently.

20. The horizontally elongate implant system for stabilizing a bony segment pair of claim 19, the lower BSIB and the upper BSIB including a bone growth material.

21. The horizontally elongate implant system for stabilizing a bony segment pair of claim 12, wherein the lower BSIB and upper BSIB are comprised substantially of polyetheretherketone.

* * * * *